(12) United States Patent
Weinberg et al.

(10) Patent No.: US 7,261,903 B1
(45) Date of Patent: Aug. 28, 2007

(54) LIPID EMULSIONS IN THE TREATMENT OF SYSTEMIC POISONING

(76) Inventors: Guy Weinberg, 9056 Karlov, Skokie, IL (US) 60076; Paul Hertz, 4320 W. Suffield Ct., Skokie, IL (US) 60076

( * ) Notice: Subject to any disclaimer, the term of this patent is extended or adjusted under 35 U.S.C. 154(b) by 0 days.

(21) Appl. No.: 09/622,816

(22) PCT Filed: Feb. 22, 1999

(86) PCT No.: PCT/US99/03805

§ 371 (c)(1),
(2), (4) Date: Jul. 17, 2001

(87) PCT Pub. No.: WO99/43301

PCT Pub. Date: Sep. 2, 1999

(51) Int. Cl.
*A61K 9/127* (2006.01)
*A61K 9/107* (2006.01)

(52) U.S. Cl. .................. 424/450; 424/400; 514/937; 514/938; 514/943

(58) Field of Classification Search .......... 424/400; 514/937–943
See application file for complete search history.

(56) References Cited

U.S. PATENT DOCUMENTS 4,183,918 A * 1/1980 Asher et al. ............. 424/94.3
4,323,563 A * 4/1982 Takami et al. ............. 514/78
5,089,268 A * 2/1992 Katz ....................... 424/450
6,139,871 A * 10/2000 Hope et al. ............... 424/450

FOREIGN PATENT DOCUMENTS

GB      2 050 799      * 1/1981

OTHER PUBLICATIONS

Cave et al. (2005), "Intralipid ameliorates thiopentone induced respiratory depression in rats: Investigative pilot study," Emergency Medicine Australasia 17:180-183.
Goor and Goor (2003), "Letter to the editor: Has the silver bullet been found?" Regional Anesthesia and Pain Medicine 29(1):73-74.
Groban and Butterworth (2003), "Lipid reversal of bupivacaine toxicity: Has the silver bullet been identified?" Regional Anesthesia and Pain Medicine 28(3):167-169.
Krieglstein et al. (1974), "Influence of emulsified fat on chlorpromazine availability in rat blood," Experientia 30:924-926.
Weinberg (2003), "Lipid emulsion infusion rescues dogs from bupivacaine-induced cardiac toxicity," Regional Anesthesia and Pain Medicine 28(3):198-202.
Weinberg (2003), "Letter to the editor: Reply to Drs. Goor, Groban, and Butterworth—Lipid Rescue: Caveats and Recommendations for the 'silver bullet'," Regional Anesthesia and Pain Medicine 29(1):74-75.

* cited by examiner

*Primary Examiner*—Gollamudi S. Kishore
(74) *Attorney, Agent, or Firm*—Greenlee, Winner, and Sullivan, P.C.

(57) ABSTRACT

Lipid emulsion compositions and methods of using such composition via intravenous infusion to reduce the bioavailability and toxicity of poisonous agents in the bloodstream.

9 Claims, 2 Drawing Sheets

LIPID EMULSIONS IN THE TREATMENT OF SYSTEMIC POISONING

FIELD OF THE INVENTION

This invention relates to lipid emulsion compositions and to methods of reducing the bioavailability and toxicity of poisons and other noxious agents present in the circulation by the intravenous infusion of a lipid emulsion composition.

BACKGROUND OF THE INVENTION

An emulsion is a collective of lipid or oil microparticles dispersed in water usually by the action of an emulsifying agent. Historically, emulsions have been widely used in the cosmetic and drug industries in connection with creams, depilatories, antiperspirants, deodorants, antiseptics and the like. Emulsion systems which include sugars, amino acids, vitamins, and electrolytes have also been utilized as a means of providing intravenous nutrition in order to maintain a patient's life when oral or nasal feeding is impossible or insufficient (see U.S. Pat. No. 5,674,527 to Inoue et al.). Another common use of emulsions is in parenteral drug delivery systems (see U.S. Pat. No. 3,538,216 to Polin et al.). These drug delivery systems feature hydrophobic medicinals suspended in an emulsion to be delivered to the patient in a sustained release manner. The lipid emulsion in this system consists of a thixotropic agent, a gelatinous-oil composition containing an ion-exchange agent, and water.

Also, edible but non-digestible emulsions have been used as traps for toxins present in the gastrointestinal (GI) tract as described in U.S. Pat. No. 4,183,918 to Asher et al. In this trap system, the emulsion is fed to a symptomatic patient wherein the toxins are removed by the action of the absorbent-containing emulsion passing through the GI tract. Key features of this system include the use of non-digestible oils as the exterior phase of the emulsion and the use of a reactant or adsorbent in the interior aqueous phase of the emulsion. Examples of exterior phase oils used in this system include highly refined hydrocarbon oils, mineral oils, and silicone oils, while preferred interior phase reactants and adsorbents include silica gel and carbon.

Other means of detoxifying the body include the delivery of liposomes containing active reagents to a patient. For example, an aqueous solution of the chelating agent EDTA was encapsulated by liposomes (synthetic membrane vesicles) and given to a patient undergoing chemotherapy in order to remove the radioactive metal plutonium from the patient's body. (Rahman et al., Science (1973) 180:300). Liposomes, in most cases, act by rupturing their membranes to release their inner contents. As such, liposomes have also been used to deliver drugs in a controlled-release manner as described in U.S. Pat. No. 4,837,028 to Allen. However, liposomes are not readily permeable to extraneous toxic agents present in the body.

Despite the foregoing, a need remains for materials and methods to effectively decrease the bioavailability and toxic substances in the bloodstream, especially those lipophilic or amphilic agents such as antidepressants, anesthetics, alcohol, or others which require immediate intervention when present in dangerous amounts.

SUMMARY OF THE INVENTION

The invention is directed to lipid emulsion compositions and methods for reducing the bioavailability and toxicity of poisonous agents in the circulation by the intravenous infusion of a lipid emulsion. Preferred lipid emulsion compositions comprise an oil, an emulsifier, a tonicity modifier, and water. In a preferred method of the invention, a patient having toxic levels of a drug or other toxic substances is intravenously infused with a composition of the lipid emulsion wherein the toxic substance permeates the emulsion and is redistributed according to its lipid:aqueous partition coefficient into the non-aqueous (lipid) phase of the emulsion, thereby decreasing the bioavailability of the toxic substance. Such lipid sinks have wide applicability to the treatment of toxicity associated with lipophilic and amphiphilic substances. In a preferred embodiment, the invention is directed to the treatment of toxicity due to lipophilic and amphiphilic substances.

In another preferred embodiment, the invention is useful in the treatment of cardiotoxicity, including those instances of cardiac arrest due to unknown toxic agents and, in particular, when the toxic agents are lipophilic and amphiphilic substances.

Yet another embodiment of the present invention comprises materials and methods for treating toxicity associated with anesthetic agents, including but not limited to, bupivacaine, lidocaine, and other anesthetic agents.

A preferred lipid emulsion composition comprises about 20 percent by weight soybean oil, about 2 weight percent glycerin, about 1 weight percent egg yolk phospholipid, and about 80 weight percent water; however, the composition can vary depending upon the nature and lipid partition coefficient of the toxic substance in the bloodstream.

In a preferred embodiment, a 20 percent by weight solution of the emulsion in water is infused intravenously at an initial rate of about 7.5 milliliters per kilogram for a time period of about 30 seconds followed by a steady-state rate of about 3 milliliters per kilogram per minute for a time period of about 2 minutes.

Other lipid-emulsions according to the present invention include emulsions comprising one or more of the following substances: glycerophospholipids such as phosphatidylcholine; cholesterol, stearylamine; phosphatidylserine; phosphotidylglycerol and other lipids. Also included within the scope of the invention are microemulsions which include oil, water, and an amphiphile system that is macroscopically mono-phasic, optically isotropic, thermodynamically stable and characterized by ultra-low interfacial tension values.

The invention is also directed to a device for the convenient administration of the emulsions of the present invention to a patient. The device is also useful for administering other therapeutic substances by way of a regimen comprising the administration of a bolus of the agent and the subsequent infusion of the agent over a period of time.

DETAILED DESCRIPTION

Figure 1:
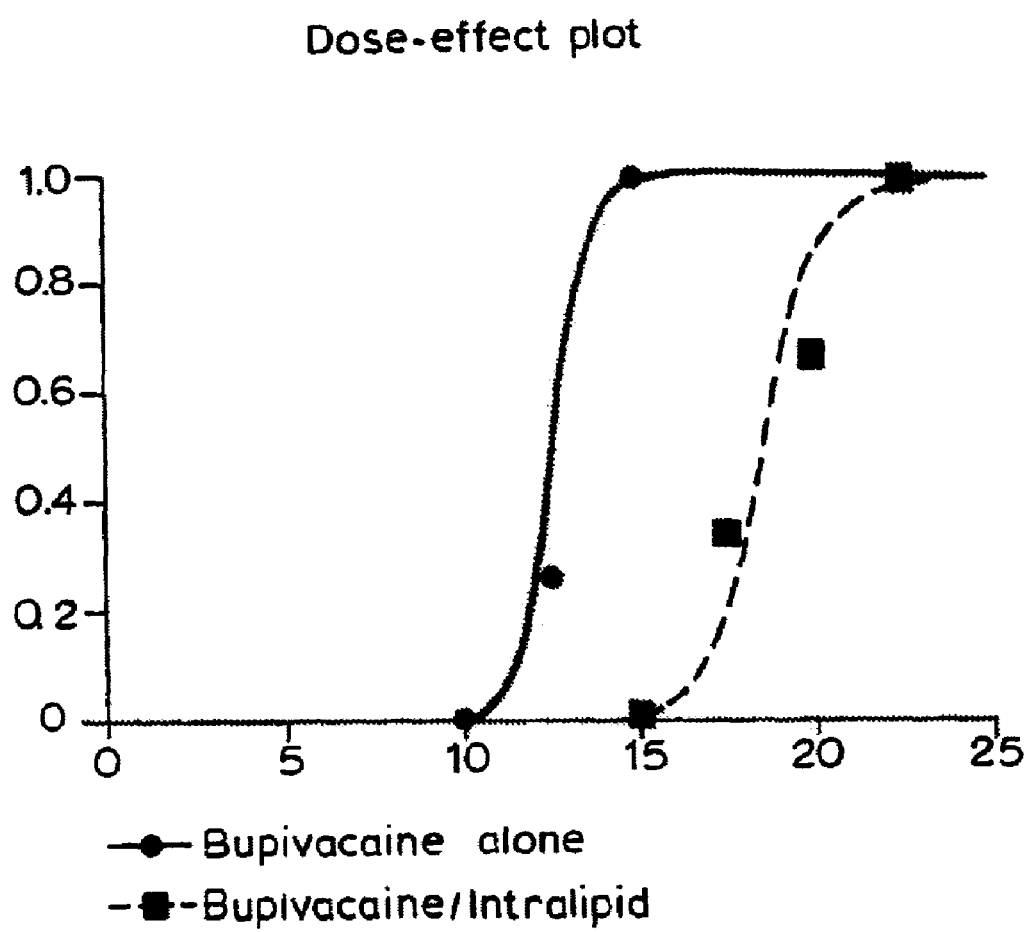
FIG. 1 is a graph depicting the probit analysis of the mortality fraction versus the bupivacaine dose for animals treated according to protocol 2 (lipid resuscitation) for intravenous infusions of either saline or a lipid emulsion composition.

The present invention relates to lipid emulsion compositions and to methods and apparatus for reducing the bioavailability and toxicity of poisonous or noxious agents present in the circulation, by intravenous administration of a lipid emulsion. A preferred method for the treatment of systemic toxicity includes making a patient in need of such therapy, rapidly lipemic by the intravenous infusion of an initial large bolus dose of an emulsion followed by a slower steady-state rate infusion of the emulsion. Although the rate of infusion can vary with respect to the particular emulsion utilized with the toxic agent involved and with the particular patient, by way of example, an initial rate of the infusion may be in the range of about 0.5 ml/kg/min to about 10 ml/kg/min for a time period of about 0.5 min followed by a steady-state rate in the range of about 0.1 ml/kg/min to about 3 ml/kg/min for a time period of about 2 minutes.

The lipid emulsion composition used to detoxify the blood comprises an oil, an emulsifier, a tonicity modifier, and water. Additional ingredients can include a surfactant, a co-solvent, a bacteriostat, a preservative, an active ingredient, and an adsorbent.

Preferably the oil in the emulsion composition is one or more oils selected from the group consisting of monoglycerides, diglycerides, triglycerides, and mixtures thereof. More preferably, the oil is a naturally occurring plant oil selected from the group consisting of soybean oil, cottonseed oil, safflower oil, corn oil, coconut oil, sesame oil, peanut oil, olive oil, and mixtures thereof. Most preferably the oil is soybean oil. In addition, the oil can be an animal oil or a fish oil such as cod liver oil. The oil can also can be a mineral oil or a chemically-synthesized oil such as 2-linoleoyl-1,3-dioctanoyl glycerol. Semisynthetic mono-, di- or triglycerides may also be used and include rac-glyceryl-1-monopalmitic, acyl glyceryl-1-monoolein, 1,2-dipalmitic, 1,3-dipalmitic, trimyristin, tripalmitin, tristearin, triolein, trilaiden and the like.

The emulsifier in the lipid emulsion composition preferably is a naturally-occurring phospholipid. Preferred phospholipids can be derived from egg or soy sources. Exemplary phospholipids include but are not limited to, egg yolk phospholipids, hydrogenated egg yolk phospholipids, soybean phospholipids, hydrogenated soybean phospholipids, and mixtures thereof. Preferably, the phospholipid is egg yolk phospholipid. The emulsifier also can be a synthetic lecithin such as dihexanoyl-L-$\alpha$-lecithin. Among the other emulsifiers useful in the practice of the present invention are other glycerophospholipids such phosphatidylcholine lipids such as cholesterol, stearylamine, phosphatidylserine, phosphatidylglycerol and other lipids.

The tonicity modifier preferably is a member of the group consisting of glycerin, sorbital, polyoxyethylated hydrocarbons, and $C_6$–$C_{20}$ saturated or unsaturated aliphatic acids. The optional co-solvent preferably is an alcohol such as isopropanol or benzyl alcohol or the like. The bacteriostat or preservative can be any of those commercially available which are non-toxic. The active ingredient can be a desired drug or reactant which can render the toxic agent non-toxic or which may act to counter the physiological effects of the toxic agent, while the adsorbent can be, for example, charcoal, silica gel, or the like.

In formulating the emulsion, the oil is preferably present in an amount in the range of about 10 to about 30 percent by weight of the composition. The surfactant in the emulsion composition is present in an amount in the range of about 1 to about 5 percent by weight of the composition. Water is present in the emulsion composition in an amount in the range of about 70 to about 90 percent by weight.

A preferred lipid emulsion composition comprises about 20 weight percent soybean oil, about 2 weight percent glycerin, about 1 weight percent egg yolk phospholipid, and about 80 weight percent water.

In the following examples, the commercially available (Healthcare, Deerfield, Ill.) lipid emulsion composition, Intralipid® was used. Intralipid® (Baxter) was introduced into the U.S. marketplace in 1975 for intravenous use. Intralipid® contains 10% w/v soybean oil as a source of polyunsaturated fatty acids, and 1.2% w/v of purified egg phospholipids which act as an emulsifying agent. The remainder of the composition is water added to achieve final lipid concentration in the range of about 10% w/v to about 30% w/v as is desired. Glycerol is added to make the lipid emulsion isotonic, with about 2.25% w/v present in Intralipid®. The pH range of the Intralipid® emulsion is from about 5.5 to 8.

The lipid emulsion can be prepared by any convenient means, such as sonication and the like. The components of the emulsion can be mixed or premixed in any order prior to the sonication process. The emulsion preferably comprises particles in the range of about 0.25 microns to about 0.75 microns in diameter.

While the invention is exemplified by way of reducing or eliminating the toxic effects of the anaesthetic, bupivacaine, it is readily apparent to one of skill in the art that lipid emulsions may also be used to treat toxicity associated with other lipophilic or amphiphilic agents including tricyclic antidepressants (e.g., amitryptiline), adriamycin, organic solvents, other anesthetic agents such as tetracaine, etidocaine and alcohol.

The methods and compositions of the present invention are applicable to several clinical scenarios in addition to treatment of acute toxicity such as is exemplified below. For example, in the situation where a patient will be receiving a known amount of toxin (e.g., a lipophilic chemotherapeutic agent such as adriamycin), an emulsion according to the invention may be administered to the patient to reduce toxicity of the agent thereby increasing its safe dose.

In another scenario, when an acutely ill patient presents with apparent toxicity or a possible overdose of a known or unknown drug, e.g., presenting with cardiac arrhythmias in a young, otherwise healthy person, or a person with a history of depression being treated with tricyclic antidepressants, the patient may be treated with an emulsion according to the present invention.

Other exemplary lipophilic toxic agents which may be sequestered using the emulsions of the present invention include gasoline, inhaled propellants, N,N-diethyl-m-toluamide (DEET).

The amount of toxin might be known precisely, or entirely unknown. In the latter case, the patient's clinical status (mildly or severely ill) will guide treatment. The length of treatment following an initial dose will be determined by clinical response against a predetermined maximum safe dose for a patient's weight, which is readily determined by routine methods. The spent emulsion will be metabolized slowly (over hours) probably by lipoprotein lipase which releases the fatty acids from the triglycerides. The toxin is then released from the emulsion droplets, but this slow release allows the patient's normal metabolism to chemically modify, excrete, or otherwise detoxify the toxin. The emulsion can be delivered via any peripheral or central vein.

The invention is described in more detail below by way of non-limiting examples. Example 1 describes the pretreatment of animals with a lipid emulsion and the effect of shifting the dose-response to bupivacaine induced asystole. Example 2 demonstrates the resuscitation of an animal from a toxic dose of bupivacaine by use of an intravenously infused lipid emulsion.

EXAMPLE 1

Pretreatment with a Lipid Emulsion Composition Shifts the Dose-Response to Bupivacaine Induced Asystole in Rats Studies were undertaken to assess the ability of a lipid emulsion to shift the dose-response to drug-induced asystole (heart stoppage) in rats. Pretreatment with a lipid emulsion increased the dose of bupivacaine (a local anaesthetic) required to induce asystole. Racemic bupivacaine hydrochloride was purchased from Sigma (St. Louis, Mo.) while tritiated bupivacaine was purchased from Moravek Biochemicals (Brea, Calif.). Intralipid® was purchased from Baxter Healthcare (Deerfield, Ill.). Male Sprague-Dawley rats weighing between about 250 grams to about 370 grams were used in all experiments.

Animals were first anesthetized in a bell jar with isoflurane to allow intubation, then mechanically ventilated with about 1.75% isoflurane in about 100% oxygen using a Harvard rodent ventilatory model 680 in conjunction with a tidal volume of 3 ml and a starting rate of about 40 breaths per minute. Catheters were inserted into the right internal jugular vein, the right carotid artery, and the right internal iliac vein. Electrocardiogram (ECG) was monitored via three subcutaneous needle electrodes in each rat. Arterial blood gas measurements were made after the induction of general anesthesia and again just prior to infusions to confirm a $pCO_2$ in the range of about 30 to about 35 mm Hg and a pH in the range of about 7.35 to about 7.45 units.

All animals were allowed to stabilize for about 15 minutes while arterial blood pressure and ECG were monitored. There were six animals in each group. Control animals (group 1) received saline intravenously as pretreatment while test animals (groups 2–4) were pretreated intravenously with the lipid emulsion composition Intralipid® at concentrations of either about 10% by weight (group 2), about 20% by weight (group 3), or about 30% by weight (group 4) in saline. All pretreatments were infused at a rate of about 3 ml/kg/min for 5 minutes via the internal jugular vein.

Immediately following pretreatment, all animals received an infusion of about 0.75% bupivacaine via the internal iliac catheter at a rate of 10 mg/kg/min to an end point of about ten seconds of asystole. Blood was then drawn from the aorta into a heparinized syringe for plasma bupivacaine determinations. The cumulative lethal dose of bupivacaine was calculated in mg/kg for all animals.

Plasma bupivacaine concentrations were determined by high performance liquid chromatograph (HPLC) after the samples had been extracted with hexane. The method of hexane extraction was validated with bupivacaine spiked samples and provided greater than about 95% recovery of bupivacaine from both normal and lipemic plasma. Thus, plasma bupivacaine concentrations reflected total bupivacaine content in both the aqueous and lipid phases of the specimen. The compounds were separated using a C18 column, 5 micrometer, 150 by 3.9 mm internal diameter (Symmetry, Waters Associates, Milford, Mass.) using the anaesthetic mepivacaine as an internal standard. The mobile phase consisted of about 25% acetonitrile in about 25 mM phosphate buffer adjusted to about pH 3.0. The flow rate was about 1 ml/min with a constant column temperature of about 30° C. The retention time for the mepivacaine internal standard was about 1.8 min. and about 4.0 min for bupivacaine during a 6 min. long run. The drugs were detected at a wavelength of about 215 nm.

The bupivacaine lipid:aqueous partition coefficient was determined for a mixture of Intralipid® and rat plasma. Blood obtained from rats by direct heart puncture under halothane anesthesia was centrifuged and the plasma was separated. Equal volumes of about 30% Intralipid® and plasma (approximately 2 ml each) were combined and vortexed. Approximately 1.0 µCi of tritiated bupivacaine (specific activity 0.81 Ci/mole) was added to the mixture to a final bupivacaine concentration of about 93 µg/ml. This mixture was vortexed again then separated into aliquots of about 1 ml. These aliquots were allowed to sit undisturbed for about one hour at about 38° C., then centrifuged at about 10,000 g for about 10 minutes. High speed centrifugation separated each of these mixtures into a clear aqueous phase (about 0.85 ml) under a lipid phase (about 0.15 ml). The latter comprised a clear layer beneath a very thin white cap. The cap was removed then redissolved in saline to a total volume of about 1 ml. Aliquots of this solution and the aqueous plasma phase were then analyzed for tritiated bupivacaine content by liquid scintillation counting. The bupivacaine lipid:aqueous partition coefficient was given by the ratio of bupivacaine in the combined lipid phase (following correction for saline dilution) to the bupivacaine in the aqueous phase. This experiment was performed in triplicate.

Bupivacaine dose and plasma concentrations were analyzed by Kruskal-Wallis one way analysis of variance on ranks. Post hoc testing of both data sets was performed by Student-Newman-Keul's method for multiple comparisons (SigmaStat, Jandel Scientific/San Rafael, Calif.). Cumulative bupivacaine dose data were nonparametric and median values were compared by differences of ranks. Plasma bupivacaine concentration data were parametric and differences in mean values were evaluated. Probit analysis (CalcuSyn, Biosoft/Cambridge, England) was used to compare bupivacaine $LD_{50}$ values in the saline and lipid portions. The difference in survival of the two groups at 15 mg/kg bupivacaine was further evaluated using a z test of proportions. Statistical significance in all experiments was taken as p less than or equal to 0.05.

The results indicate that the lethal bupivacaine dose among all animals ranged from about 12.7 mg/kg in an animal receiving saline pretreatment to about 111 mg/kg in an animal receiving an emulsion composition containing about 30% Intralipid®. Median bupivacaine lethal doses were as follows: (mg/kg; $25^{th}$ percentile-75th percentile): Group 1 (saline) 17.8, 13.2–20.3; Group 2 (10% Intralipid®) 27.6, 22.2–31.7; Group 3 (20% Intralipid®) 49.8, 41.2–57.8; Group 4 (30% Intralipid®) 82.0, 71–3–101. Statistical significance for differences in median lethal bupivacaine does was achieved between all groups (p less than 0.001).

The mean plasma bupivacaine concentrations at the time of asystole for protocol 1 were (mcg/ml+/−standard error of the mean): group 1, 93.3+/−7.6; group 2, 115+/−15; group 3, 177+/−31; and group 4, 212+/−45. Statistical significance was achieved for the difference in mean concentrations between groups 1 and 4.

Probit analysis of the data from protocol provided the following bupivacaine $LD_{50}$ values for the two treatment groups [lower and upper 95% confidence intervals (mg/kg): saline, 12.5, 11.8–13-4; lipid, 18.5, 17.8–19.3]. A z test of proportions at 15 mg/kg bupivacaine showed significance in the difference in survival between the two groups at this dose (p less than 0.004).

The lipid:aqueous ratio of bupivacaine concentrations (+/−standard error) was 11.9+/−1.77. When equal volumes of a solution of about 30% by weight Intralipid® and plasma were combined, the actual lipid volume was about 15% of total, and the percent of total bupivacaine dissolved in the lipid phase of this mixture (+/−standard error) was about 75.3%+/−1.32%.

EXAMPLE 2

Resuscitation from a Toxic Dose of Bupivacaine with a Lipid Emulsion Composition Experiments were performed to evaluate the ability of a lipid emulsion to resuscitate an animal from a toxic dose of bupivacaine. All animals were anaesthetized, instrumented and stabilized at about 1.75% isoflurane as described in Experiment 1, and arterial blood pressure and ECG were continuously monitored. Each rat received an intravenous dose of bupivacaine (see below for doses) for more than about 10 seconds by Harvard infusion pump, via the iliac catheter. Immediately after the bupivacaine dose, isoflurane was stopped and mechanical ventilation was continued with about 100% oxygen, with all animals receiving an infusion of either saline or about 30% by wt. solution of Intralipid® via the internal jugular catheter. In each case, the initial infusion rate was about 7.5 ml/kg bolus over 30 seconds, followed by a steady-state rate of about 3 ml/kg/min for about 2 minutes. Chest compressions were given during infusion for any animal experiencing more than about 15 seconds of asystole. Survival was scored about 5 minutes after the bupivacaine bolus and required both heart rate greater than about 100 beats per minute and systolic blood pressure greater than about 60 mmHg. Isoflurane at a concentration of about 1.75% was restarted whenever the blood pressure or heart rate met the survival criteria. Thus, a difference in survival between control and treated animals required rapid reversal of the cardiotoxic effects of a potentially fatal bupivacaine dose.

Preliminary experiments with this protocol established the bupivacaine bolus dose ranges necessary to achieve groups with 100% survival, 100% mortality and at least one intervening dose for both control and lipid treatment. These were 10 mg/kg, 12.5 mg/kg, and 15 mg/kg for the controls and 15 mg/kg, 17.5 mg/kg, 20 mg/kg and 22.5 mg/kg for lipid treated animals.

This resuscitation protocol provided a stringent test of efficacy of the lipid emulsion composition in treating bupivacaine induced cardiovascular collapse. The short fixed injection interval (10 seconds) modeled the clinical occurrence of a rapid intravascular bupivacaine injection. The experimental results showed about 48% increase in the bupivacaine $LD_{50}$ when resuscitation included lipid infusion (from about 12.5 mg/kg to 18.5 mg/kg). At 15 mg/kg, a usually fatal bupivacaine dose, the lipid infused animals survived.

As illustrated by the foregoing results, lipid infusion reduces bupivacaine-associated cardiotoxicity. Partition experiments suggest that the primary benefit of lipid infusion results from a lipid sink effect where the poison is drawn from the blood into the non-aqueous component of the emulsion thereby reducing the amount of toxin in the cells such that toxicity is reversed. Other mechanisms may also be active. These observations suggest that the use of intravenously infused lipid emulsions can reverse toxic effects, particularly the cardiotoxic effects of lipophilic or ampiphilic agents. An important parameter in the design of such emulsion compositions is the partition coefficient of the toxic agent in the emulsion which can be readily determined by methods such as those described above.

EXAMPLE 3

Emulsion Delivery Device

Figure 2:
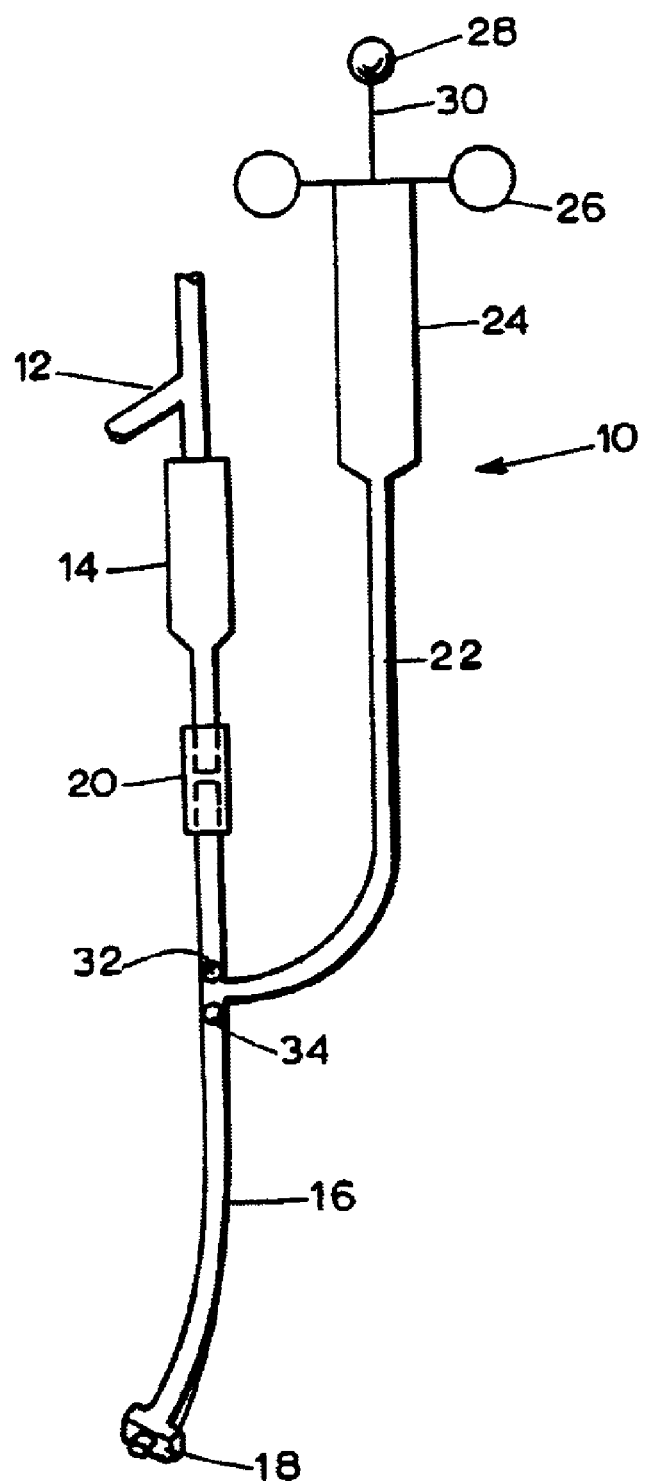
FIG. 2 depicts a device for administering to a patient the emulsions of the present invention.

A delivery device 10 constructed in accordance with the teachings of the invention is illustrated in FIG. 2. As shown in that figure, the delivery device 10 includes a vented spike 12 for insertion into an intralipid (lipid emulsion)-containing bottle or other suitable container (not shown) suspended from an IV pole in a conventional manner. The vented spike 12 is in communication with a drip chamber 14 which is, in turn, in communication with a main delivery channel implemented by a length of tubing 16 which preferably has a large bore. The bottom end of the tubing 16 is provided with a connecting means, which preferably is a conventional luer lock 18.

To control the flow of fluid from the drip chamber 14, the delivery device 10 is provided with a conventional roller clamp 20 but other means for regulating fluid flow are also contemplated. The roller clamp 20 operatively engages the outer surface of the tubing 16 immediately below the drip chamber 14. By adjusting the roller clamp 18, health care personnel can regulate the rate at which fluid exits the drip chamber 14.

In accordance with one aspect of the invention, the delivery device 10 is provided with a length of extension tubing 22. As shown in FIG. 2, one end of the extension tubing 22 is in fluid communication with the large bore tubing 16. The extension tubing 22 may be integrally formed with or otherwise connected with the large bore tubing 16. The opposite end of the extension tube 22 is coupled to a syringe 24. The syringe 24 is preferably implemented with one or more finger rings 26 and a thumb ring 28 on its piston 30. Significantly, the syringe 24 can be suspended from the IV pole by its thumb ring 28. Suspending the syringe 24 in this manner prevents the extension tubing 22 and the syringe 24 from kinking when the injection fluid (emulsion) is just dripping and not being pushed from the syringe 24 via the piston 30.

For the purpose of controlling the direction of fluid flow through the device 10, the delivery device is provided with two one-way valves 32, 34. Preferably ball valves are utilized in the invention. As shown in FIG. 2, a first one of the ball valves 32 is located above the junction of the large bore tubing 16 and the extension tube 22. This ball valve 32 prevents fluid flowing through the extension tube 22 from backing up the large bore tubing 16 towards the drip chamber 14. The second ball valve 32 is located below the junction of the large bore tubing 16 and the extension tube 22. This second ball valve 34 prevents fluid from passing back up the main delivery channel towards the syringe 24.

Preferably, the thumb ring 28 of the syringe 24 is suspended from the IV pole at substantially the same height as the top of the intralipid bottle. As a result, the length of the extension tubing 22 is preferably defined by the distance from the ball valve 32 to the IV pole. This distance is, in turn, defined by the length of the tubing 16 from the vented spike 12 to the ball valve 32 and the length of the intralipid bottle. Preferably, the length of the extension tubing 22 is selectively within these parameters to avoid any kinking when the syringe 24 is suspended from the IV pole.

While the above-described delivery device is particularly useful for administering the emulsions of the present invention, it is readily apparent that it may also be used to administer therapeutic or prophylactic substances.

The foregoing is intended to be illustrative of the invention but not limiting. Numerous variations and modifications of the present invention may be effected without departing from the spirit and scope of the invention.

All of the references cited herein are incorporated by reference in their entirety.

We claim:

1. A method for treating cardiotoxicity caused by a lipophilic or amphiphilic anesthetic agent, which comprises infusing a lipid emulsion composition intravenously whereby the anesthetic agent permeates the lipid emulsion composition and is withdrawn from the bloodstream, said lipid emulsion comprising soybean oil, an emulsifier, a tonicity modifier, and water, wherein the soybean oil is present in an amount in the range of about 10 to about 30 percent by weight, the water is present in an amount in the range of about 70 to about 90 percent by weight, and the emulsifier is present in an amount in the range of about 1 percent to about 5 percent by weight, wherein said anesthetic agent is selected from the group consisting of bupivacaine, lidocaine, tetracaine, and etidocaine.

2. The method of claim 1 wherein the lipid emulsion composition comprises about 20 weight percent oil, where the oil is soybean oil, about 2 weight percent tonicity modifier, where the tonicity modifier is glycerin, and about 1 weight percent emulsifier, where the emulsifier is egg yolk phospholipids, and about 80 weight percent water.

3. The method of claim 1 wherein the lipid emulsion composition is intravenously infused at an initial rate in the range of about 7.5 milliliters per kilogram per minute for a time period of about 30 seconds followed by a steady-state rate in the range of about 3 milliliters per kilogram per minute for a time period of about 2 minutes.

4. The method of claim 1 wherein the emulsifier is a phospholipid.

5. The method of claim 4 wherein the phospholipid is selected from the group comprising of egg yolk phospholipids, hydrogenated egg yolk phosphor lipids, soybean phospholipids, hydrogenated soybean phospholipids, and mixtures thereof.

6. The method of claim 1 wherein the emulsifier is a lecithin.

7. The method of claim 1 wherein the tonicity modifier is selected from the group consisting of glycerin, sorbital, polyoxyethylated hydrocarbons, and $C_6$–$C_{20}$ saturated or unsaturated aliphatic acids.

8. The method of claim 1 wherein the tonicity modifier comprises glycerin.

9. The method of claim 1 wherein the emulsion comprises particles in the range of about 0.25 microns to about 0.75 microns in diameter.

* * * * *